United States Patent [19]

Maegawa et al.

[11] Patent Number: 4,670,488
[45] Date of Patent: Jun. 2, 1987

[54] PIPERIDINE DERIVATIVES, THEIR PRODUCTION AND USE AS STABILIZERS

[75] Inventors: Yuzo Maegawa, Osaka; Yukoh Takahashi, Toyonaka; Eizo Okino, Kurashiki; Tatsuo Kaneoya, Toyonaka; Haruki Okamura, Osaka; Shinichi Yachigo, Toyonaka; Tamaki Ishii, Suita, all of Japan

[73] Assignee: Sumitomo Chemical Co., Ltd., Osaka, Japan

[21] Appl. No.: 805,380

[22] Filed: Dec. 4, 1985

[30] Foreign Application Priority Data

Dec. 28, 1984 [JP] Japan ................ 59-275481

[51] Int. Cl.$^4$ .................... C07D 401/12; C07K 5/34
[52] U.S. Cl. ................... 524/103; 524/102; 524/99; 546/188; 546/216; 546/223
[58] Field of Search ........... 546/216, 223, 188; 524/99, 102, 103

[56] References Cited

U.S. PATENT DOCUMENTS 4,578,472  3/1986  Yoshimura et al. ............ 546/188

Primary Examiner—Robert T. Bond

[57] ABSTRACT

The present invention relates to a piperidine derivative represented by the general formula (I),

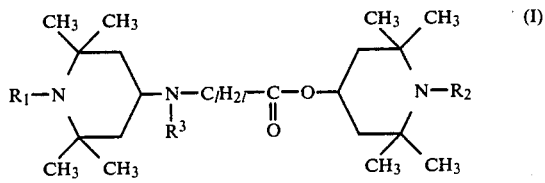

wherein $R_1$ and $R_2$ independently represent a hydrogen atom or a $C_1$–$C_3$ alkyl or $C_2$–$C_{20}$ acyl group, $R_3$ represents a hydrogen atom or a $C_1$–$C_{20}$ alkyl, $C_6$–$C_{20}$ aryl, $C_7$–$C_{20}$ aralkyl or $C_2$–$C_{20}$ acyl group, and l represents 1 to 3, and a stabilizer for organic substances containing said piperidine derivative as an effective ingredient.

14 Claims, No Drawings

PIPERIDINE DERIVATIVES, THEIR PRODUCTION AND USE AS STABILIZERS

The present invention relates to a piperidine derivative represented by the general formula (I),

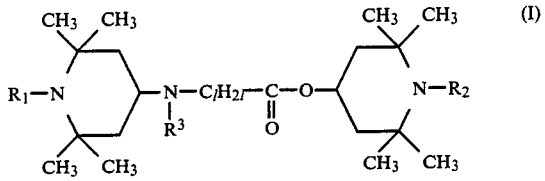

wherein $R_1$ and $R_2$ independently represent a hydrogen atom or a $C_1$–$C_3$ alkyl or $C_2$–$C_{20}$ acyl group, $R_3$ represents a hydrogen atom or a $C_1$–$C_{20}$ alkyl, $C_6$–$C_{20}$ aryl, $C_7$–$C_{20}$ aralkyl or $C_2$–$C_{20}$ acyl group, and $l$ represents 1 to 3, its production and a stabilizer for organic substances containing, said piperidine derivative as an effective ingredient.

It is well known that synthetic resins such as polyethylene, polypropylene, polyvinyl chloride, polyurethane, ABS resin, etc. and organic substances such as paints deteriorate in quality by the action of light, thereby showing a remarkable reduction in the physical properties accompanied by such phenomena as softening, embrittlement, discoloration and the like.

For the purpose of preventing such deterioration by light, it is so far known to use various kinds of light stabilizers such as 2-hydroxy-4-methoxybenzophenone, 2-hydroxy-4-n-octoxybenzophenone, 2-(2-hydroxy-5-methylphenyl)benzotriazole, 2-(2-hydroxy-3-tert-butyl-5-methylphenyl)-5-chlorobenzotriazole, 2-(2-hydroxy-3,5-dipentylphenyl)-benzotriazole, ethyl 2-cyano-3,3-diphenylacrylate, 2,4-di-tert-butylphenyl 3,5-di-tert-butyl-4-hydroxybenzoate, [2,2'-thiobis(4-tert-octylphenolate)]-n-butylamine.nickel (II), Ni salt of bis(3,5-di-tert-butyl-4-hydroxybenzylphosphoric acid monoethyl ester), bis (2,2,6,6-tetramethyl-4-piperidinyl)sebacate and the like. These light stabilizers, however, are not yet quite satisfactory in terms of light fastness.

The present inventors extensively studied to solve these problems, and as a result, found that the piperidine derivative represented by the foregoing general formula (I) has excellent effects in preventing organic substances, such as synthetic resins, paints, etc. from deterioration by light. The present inventors thus attained the present invention as a result of these studies.

The present inventors were the first to synthesize said piperidine derivative of the present invention, and it can be produced by reacting a carboxylic acid derivative represented by the general formula (II),

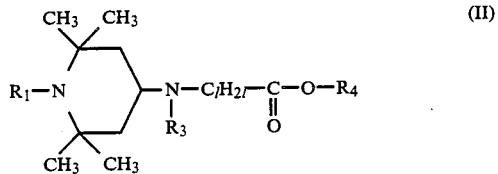

wherein $R_1$, $R_3$ and $l$ have the same meanings as described above, and $R_4$ represents a hydrogen atom or a $C_1$–$C_3$ alkyl group, with a piperidinol represented by the general formula (III),

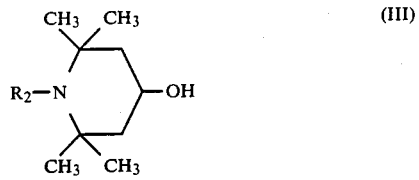

wherein $R_2$ has the same meaning as described above.

Examples of $R_1$ and $R_2$ include a hydrogen atom, alkyl groups (e.g. methyl, ethyl, isopropyl, n-propyl) and acyl groups (e.g. acetyl, propionyl, valeryl, palmitoyl, stearoyl, oleoyl). Examples of $R_3$ include a hydrogen atom, a straight-chain, branched and cyclic alkyl groups (e.g. methyl, ethyl, propyl, butyl, cyclohexyl, octyl, ethylhexyl, isooctyl, decyl, dodecyl, tetradecyl, octadecyl), aryl groups (e.g. phenyl, tolyl, xylyl, butylphenyl, nonylphenyl, naphthyl), aralkyl groups (e.g. benzyl, phenylethyl, phenylpropyl, diphenylethyl, naphthylethyl), and acyl groups derived from carboxylic acids such as acetic acid, propionic acid, butyric acid, octylic acid, lauric acid, palmitic acid, stearic acid, benzoic acid, toluic acid, 2,2,6,6-tetramethylpiperidine-4-carboxylic acid, 3,5-di-tert-butyl-4-hydroxybenzoic acid, 3-(3,5-di-tert-butyl-4-hydroxyphenyl)propionic acid, 3-(3-methyl-5-tert-butyl-4-hydroxyphenyl)propionic acid, etc.

Examples of $R_4$ include a hydrogen atom and alkyl groups (e.g. methyl, ethyl, n-propyl, isopropyl). Examples of —$C_lH_{2l}$— include alkylene groups such as methylene, ethylene, isopropylene, trimethylene, etc.

In producing the piperidine derivative (I) of the present invention, the reaction is generally carried out with or without a solvent in the presence of a basic or acid catalyst.

When the solvent is used, there are given solvents such as aliphatic hydrocarbons (e.g. hexane, heptane, octane, nonane, decane), aromatic hydrocarbons (e.g. benzene, toluene, xylene) and alicyclic hydrocarbons (e.g. cyclohexane). These solvents may be used in mixture of two or more solvents.

When the basic catalyst is used, there are given catalysts such as metal hydroxides (e.g. sodium hydroxide, potassium hydroxide, lithium hydroxide), hydrides (e.g. sodium borohydride, sodium hydride, lithium hydride), metal amides (e.g. sodium amide, lithium amide), alkali metal alkoxides and alkali metal phenoxides (e.g. potassium tert-butoxide, sodium methoxide, sodium phenoxide) and the like. Preferred catalysts among them are potassium tert-butoxide and lithium amide.

When the acid catalyst is used, there are given catalysts such as mineral acids (e.g. hydrochloric acid, sulfuric acid, nitric acid, phosphoric acid), aromatic sulfonic acids (e.g. benzenesulfonic acid, toluenesulfonic acid, naphthalenesulfonic acid) and aliphatic sulfonic acids (e.g. methanesulfonic acid, ethanesulfonic acid).

In the reaction of the carboxylic acid derivative (II) with piperidinol (III), the amount of the latter (III) used is 0.9 to 2 moles, preferably 1.0 to 1.5 moles based on 1 mole of the former (II). The catalyst is used in an amount of 0.05 to 1.20 moles based on 1 mole of the former (II).

The reaction temperature is generally in a range of 50° to 200° C. After completion of the reaction, the desired product is separated from the reaction mixture, for example, by adding water to the reaction mixture, followed by neutralization and removal of the solvent from the organic layer. If necessary, the separated product may be purified by methods such as recrystallization with suitable solvents, and the like.

The piperidine derivative of the present invention thus obtained includes the followings:

N-(2,2,6,6-tetramethyl-4-piperidinyl)glycine(2,2,6,6-tetramethyl-4-piperidinyl)ester N-(1,2,2,6,6-pentamethyl-4-piperidinyl)-glycine(1,2,2,6,6-pentamethyl-4-piperidinyl)ester N-(2,2,6,6-tetramethyl-4-piperidinyl)-N-methylglycine(2,2,6,6-tetramethyl-4-piperidinyl)ester N-(1,2,2,6,6-pentamethyl-4-piperidinyl)-N-methylglycine(1,2,2,6,6-pentamethyl-4-piperidinyl)ester N-(2,2,6,6-tetramethyl-4-piperidinyl)-N-ethylglycine(2,2,6,6-tetramethyl-4-piperidinyl)ester N-(2,2,6,6-tetramethyl-4-piperidinyl)-N-isopropylglycine(2,2,6,6-tetramethyl-4-piperidinyl)ester N-(2,2,6,6-tetramethyl-4-piperidinyl)-N-n-hexylglycine(2,2,6,6-tetramethyl-4-piperidinyl)ester N-(2,2,6,6-tetramethyl-4-piperidinyl)-N-n-octylglycine(2,2,6,6-tetramethyl-4-piperidinyl)ester N-(2,2,6,6-tetramethyl-4-piperidinyl)-N-n-undecanylglycine(2,2,6,6-tetramethyl-4-piperidinyl)ester N-(2,2,6,6-tetramethyl-4-piperidinyl)-N-benzoylglycine(2,2,6,6-tetramethyl-4-piperidinyl)ester N-(1,2,2,6,6-pentamethyl-4-piperidinyl)-N-acetylglycine(1,2,2,6,6-pentamethyl-4-piperidinyl)ester N-(1-acetyl-2,2,6,6-tetramethyl-4-piperidinyl)-N-methylglycine(1-acetyl-2,2,6,6-tetramethyl-4-piperidinyl)ester N-(1-benzoyl-2,2,6,6-tetramethyl-4-piperidinyl)-N-ethylglycine(1-benzoyl-2,2,6,6-tetramethyl-4-piperidinyl)ester N-(1-ethyl-2,2,6,6-tetramethyl-4-piperidinyl)-N-ethylglycine(1-ethyl-2,2,6,6-tetramethyl-4-piperidinyl)ester N-(1-benzyl-2,2,6,6-tetramethyl-4-piperidinyl)-N-benzylglycine(1-benzyl-2,2,6,6-tetramethyl-4-piperidinyl)ester N-(1-propyl-2,2,6,6-tetramethyl-4-piperidinyl)-N-methylglycine(1-propyl-2,2,6,6-tetramethyl-4-piperidinyl)ester N-(1-acetyl-2,2,6,6-tetramethyl-4-piperidinyl)glycine 1-acetyl-(2,2,6,6-tetramethyl-4-piperidinyl)ester N-(2,2,6,6-tetramethyl-4-piperidinyl)aminopropionic acid(2,2,6,6-tetramethyl-4-piperidinyl)ester N-(2,2,6,6-tetramethyl-4-piperidinyl)alanine(2,2,6,6-tetramethyl-4-piperidinyl)ester N-(1,2,2,6,6-pentamethyl-4-piperidinyl)-N-benzylglycine(1,2,2,6,6-pentamethyl-4-piperidinyl)ester N-(2,2,6,6-tetramethyl-4-piperidinyl)-N-octylphenylglycine(2,2,6,6-tetramethyl-4-piperidinyl)ester N-(2,2,6,6-tetramethyl-4-piperidinyl)glycine(1,2,2,6,6-pentamethyl-4-piperidinyl)ester N-(1-acetyl-2,2,6,6-tetramethyl-4-piperidinyl)-glycine(1,2,2,6,6-pentamethyl-4-piperidinyl)ester N-(2,2,6,6-tetramethyl-4-piperidinyl)aminobutanoic acid (2,2,6,6-tetramethyl-4-piperidinyl)ester When the piperidine derivative of the present invention is used as a stabilizer for organic substances, its amount blended with the substances is generally 0.01 to 5 parts by weight, preferably 0.05 to 2 parts by weight based on 100 parts by weight of the organic substances. For blending these materials, a well-known apparatus and method for incorporating stabilizers, pigments, fillers, etc. in organic substances may be used.

In using the stabilizer for organic substances of the present invention, other additives such as antioxidants, light stabilizers, metal deactivators, metal soaps, nucleating agents, lubricants, antistatic agents, flame retardants, pigments, fillers and the like may be used.

Particularly, the thermal stability and oxidation stability of organic substances can be improved by using a phenolic type antioxidant together. Such antioxidant includes for example 2,6-di-tert-butyl-4-methylphenol, n-octadecyl $\beta$-(3,5-di-tert-butyl-4-hydroxyphenyl)propionate, 1,1,3-tris(2-methyl-4-hydroxy-5-tert-butylphenyl)butane, 1,3,5-trimethyl-2,4,6-tris(3,5-di-tert-butyl-4-hydroxybenzyl)benzene, 1,3,5-tris(3,5-di-tert-butyl-4-hydroxybenzyl)-isocyanulate, 1,3,5-tris[$\beta$-(3,5-di-tert-butyl-4-hydroxyphenyl)-propionyloxyethyl]isocyanulate, 1,3,5-tris(2,6-dimethyl-3-hydroxy-4-tert-butylbenzyl)isocyanulate, pentaerythritol tetrakis[$\beta$-(3,5-di-tert-butyl-4-hydroxyphenyl)propionate] and the like.

Also, the color of the organic substances may be improved by using a phosphite type antioxidant together. Such antioxidant includes for example tris(nonylphenyl)phosphite, distearyl pentaerythritol diphosphite, tris(2,4-di-tert-butylphenyl)phosphite, tris(2-tert-butyl-4-methylphenyl)phosphite, bis(2,4-di-tert-butylphenyl)pentaerythritol diphosphite, tetrakis(2,4-di-tert-butylphenyl)4,4'-biphenylene diphosphonite and the like.

Further, a sulfur-containing antioxidant may be used together. Such antioxidant includes for example dilauryl thiodipropionate, dimyristyl thiodipropionate, distearyl thiodipropionate, pentaerythritol tetrakis($\beta$-laurylthiopropionate), pentaerythritol tetrakis($\beta$-hexylthiopropionate) and the like.

Organic substances which can be stabilized by the piperidine derivatives of the present invention include for example low-density polyethylene, high-density polyethylene, linear low-density polyethylene, chlorinated polyethylene, EVA resin, polypropylene, polyvinyl chloride, methacrylic resin, polystyrene, impact-resistant polystyrene, ABS resin, AES resin, MBS resin, polyethylene terephthalate, polybutylene terephthalate, polyamide, polyimide, polycarbonate, polyacetal, polyurethane, unsaturated polyester resin, oil paints, spirit paints, cellulose derivative paints, synthetic resin paints, synthetic resin emulsion paints, water-based baking paints and the like.

The present invention will be illustrated in detail with reference to the following examples, but it is not limited to these examples.

EXAMPLE 1

To a four-necked flask equipped with a thermometer, a stirrer and a Deanstark trap were added 22 g (0.1 mole) of N-(2,2,6,6-tetramethyl-4-piperidinyl)glycine methyl ester, 17.3 g (0.11 mole) of 2,2,6,6-tetramethyl-4-piperidinol, 0.23 g (0.01 mole) of lithium amide and 100 g of n-heptane. The temperature was raised with stirring, and reaction was carried out at 98° to 102° C. for 6 hours, during which methanol was removed from the reaction system by means of the Deanstark trap.

After completion of the reaction, water was added to the reaction solution to dissolve the product in the n-heptane. The n-heptane layer was separated, and n-heptane in the layer was removed by distillation to obtain 26.4 g of N-(2,2,6,6-tetramethyl-4-piperidinyl)-glycine(2,2,6,6-tetramethyl-4-piperidinyl)ester as a white solid. Yield, 75% based on N-(2,2,6,6-tetramethyl-4-piperidinyl)-glycine methyl ester. Melting point, 105°–107° C. FD-mass analysis:

A parent ion peak (353) was confirmed.

| Elementary analysis (for $C_{20}H_{39}N_3O_2$): | | | |
|---|---|---|---|
| | C (%) | H (%) | N (%) |
| Found | 68.01 | 11.21 | 11.90 |
| Calculated | 67.94 | 11.12 | 11.89 |

EXAMPLE 2

To the same flask as used in Example 1 were added 28.4 g (0.1 mole) of N-(2,2,6,6-tetramethyl-4-piperidinyl)-N-n-butylglycine methyl ester, 17.3 g (0.11 mole) of 2,2,6,6-tetramethyl-4-piperidinol, 0.23 g (0.01 mole) of lithium amide and 100 g of n-octane. The temperature was raised with stirring, and reaction was carried out at 128° to 130° C. for 5 hours, during which methanol was removed from the reaction system by means of the Deanstark trap. After completion of the reaction, water was added to the reaction solution to dissolve the product in the n-octane. The n-octane layer was separated, and n-octane in the layer was removed by distillation to obtain 33.1 g of N-(2,2,6,6-tetramethyl-4-piperidinyl)-N-n-butylglycine(2,2,6,6-tetramethyl-4-piperidinyl)ester as a brown oily product. Yield, 81% based on N-(2,2,6,6-tetramethyl-4-piperidinyl)-N-n-butylglycine methyl ester.

The desired product after purification by column chromatographic separation was of a pale brown oily form.

FD-mass analysis: A parent ion peak (409) was confirmed.

| Elementary analysis (for $C_{24}H_{47}N_3O_2$): | | | |
|---|---|---|---|
| | C (%) | H (%) | N (%) |
| Found | 70.40 | 11.50 | 10.23 |
| Calculated | 70.37 | 11.56 | 10.26 |

EXAMPLE 3

To the same flask as used in Example 1 were added 34 g (0.1 mole) of N-(2,2,6,6-tetramethyl-4-piperidinyl)-N-octylglycine methyl ester, 17.3 g (0.11 mole) of 2,2,6,6-tetramethyl-4-piperidinol, 1.2 g of potassium tert-butoxide and 100 g of heptane. The temperature was raised with stirring, and reaction was carried out at 98° to 105° C. for 6 hours, during which methanol was removed from the reaction system by means of the Deanstark trap. After completion of the reaction, water was added to the reaction solution to dissolve the product in the heptane layer. The heptane layer was separated, and heptane in the layer was removed by distillation to obtain 34.3 g of N-(2,2,6,6-tetramethyl-4-piperidinyl)-N-octylglycine(2,2,6,6-tetramethyl-4-piperidinyl)ester as a pale brown oily product. Yield, 74% based on N-(2,2,6,6-tetramethyl-4-piperidinyl)-N-octylglycine methyl ester.

The desired product after purification by column chromatographic separation was of a pale yellow oily form.

FD-mass analysis: A parent ion peak (465) was confirmed.

| Elementary analysis (for $C_{28}H_{55}N_3O_2$): | | | |
|---|---|---|---|
| | C (%) | H (%) | N (%) |
| Found | 72.20 | 11.85 | 9.00 |
| Calculated | 72.21 | 11.90 | 9.02 |

EXAMPLE 4

To the same flask as used in Example 1 were added 39.4 g (0.1 mole) of N-(2,2,6,6-tetramethyl-4-piperidinyl)-N-undecanylglycine methyl ester, 17.3 g (0.11 mole) of 2,2,6,6-tetramethyl-4-piperidinol, 0.23 g of lithium amide and 100 g of heptane. The temperature was raised with stirring, and reaction was carried out at 98° to 105° C. for 6 hours, during which methanol was removed from the reaction system by means of the Deanstark trap. After completion of the reaction, water was added to the reaction solution to dissolve the product in the heptane layer. The heptane layer was separated, and heptane in the layer was removed by distillation to obtain 32.1 g of N-(2,2,6,6-tetramethyl-4-piperidinyl)-N-undecanylglycine(2,2,6,6-tetramethyl-4-piperidinyl)ester as a pale brown liquid. Yield, 61% based on N-(2,2,6,6-tetramethyl-4-piperidinyl)-N-undecanylglycine methyl ester.

A pale yellow oily product was obtained by column chromatographic separation.

FD-mass analysis: A parent ion peak (508) was confirmed.

| Elementary analysis (for $C_{31}H_{61}N_3O_2$): | | | |
|---|---|---|---|
| | C (%) | H (%) | N (%) |
| Found | 73.40 | 12.01 | 8.29 |
| Calculated | 73.32 | 12.11 | 8.27 |

EXAMPLE 5

To the same flask as used in Example 1 were added 24.2 g (0.1 mole) of N-(1,2,2,6,6-pentamethyl-4-piperidinyl)glycine methyl ester, 18.7 g (0.11 mole) of 1,2,2,6,6-pentamethyl-4-piperidinol, 0.23 g of lithium amide and 100 g of heptane. The temperature was raised with stirring, and reaction was carried out at 98° to 105° C. for 6 hours, during which methanol was removed from the reaction system by means of the Deanstark trap. After completion of the reaction, water was added to the reaction solution to dissolve the product in the heptane layer. The heptane layer was separated, and heptane in the layer was removed by distillation to obtain 30 g of N-(1,2,2,6,6-pentamethyl-4-piperidinyl)-glycine(1,2,2,6,6-pentamethyl-4-piperidinyl)ester as a pale yellow liquid. Yield, 79% based on N-(1,2,2,6,6-pentamethyl-4-piperidinyl)glycine methyl ester. A pale yellow oily product was obtained by the subsequent column chromatographic separation.

FD-mass analysis: A parent ion peak (380) was confirmed.

| Elementary analysis (for $C_{22}H_{43}N_3O_2$): | | | |
|---|---|---|---|
| | C (%) | H (%) | N (%) |
| Found | 69.31 | 11.40 | 11.10 |
| Calculated | 69.24 | 11.36 | 11.01 |

EXAMPLE 6

To the same flask as used in Example 1 were added 24.4 g (0.1 mole) of N-(2,2,6,6-tetramethyl-4-piperidinyl)aminopropionic acid methyl ester, 17.3 g (0.11 mole) of 2,2,6,6-tetramethyl-4-piperidinol, 0.23 g of lithium amide and 100 g of heptane. The temperature was raised with stirring, and reaction was carried out at 98° to 105° C. for 6 hours, during which methanol was removed from the reaction system by means of the Deanstark trap. After completion of the reaction, water was added to the reaction solution to dissolve the product in the heptane layer. The heptane layer was separated, and heptane in the layer was removed by distillation to obtain 28 g of N-(2,2,6,6-tetramethyl-4-piperidinyl)aminopropionic acid (2,2,6,6-tetramethyl-4-piperidinyl)ester as a pale yellow liquid. Yield, 73.5% based on N-(2,2,6,6-tetramethyl-4-piperidinyl)aminopropionic acid methyl ester. A pale yellow oily product was obtained by the subsequent column chromatographic separation.

FD-mass analysis: A parent ion peak (381) was confirmed.

| Elementary analysis (for $C_{22}H_{43}N_3O_2$): | | | |
|---|---|---|---|
| | C (%) | H (%) | N (%) |
| Found | 69.28 | 11.40 | 11.05 |
| Calculated | 69.24 | 11.36 | 11.01 |

EXAMPLE 7

To a four-necked flask equipped with a thermometer, a stirrer and a Deanstark trap were added 27 g (0.1 mole) of N-(1-acetyl-2,2,6,6-tetramethyl-4-piperidinyl)glycine methyl ester, 21.9 g (0.11 mole) of 1-acetyl-2,2,6,6-tetramethyl-4-piperidinol, 0.23 g of lithium amide and 100 g of heptane. The temperature was raised with stirring, and reaction was carried out at 98° to 105° C. for 6 hours, during which methanol was removed from the reaction system by means of the Deanstark trap. After completion of the reaction, the reaction solution was cooled, and water was added thereto to dissolve the product in the heptane layer. The heptane layer was separated and concentrated by removing heptane by distillation. The residue was purified by column chromatographic separation to obtain 32 g of N-(1-acetyl-2,2,6,6-tetramethyl-4-piperidinyl)-glycine(1-acetyl-2,2,6,6-tetramethyl-4-piperidinyl)ester as a pale yellow liquid. Yield, 73% based on N-(1-acetyl-2,2,6,6-tetramethyl-4-piperidinyl)-glycine methyl ester.

FD-mass analysis: A parent ion peak (437) was confirmed.

| Elementary analysis (for $C_{24}H_{43}N_3O_4$): | | | |
|---|---|---|---|
| | C (%) | H (%) | N (%) |
| Found | 66.00 | 9.80 | 9.55 |
| Calculated | 65.90 | 9.84 | 9.61 |

EXAMPLE 8

To a four-necked flask equipped with a thermometer, a stirrer and a Deanstark trap were added 31.8 g (0.1 mole) of N-(1,2,2,6,6-pentamethyl-4-piperidinyl)-N-benzylglycine, 20.5 g (0.12 mole) of 1,2,2,6,6-pentamethyl-4-piperidinol, 17.2 g (0.10 mole) of p-toluenesulfonic acid and 150 g of n-heptane. The temperature was raised with stirring, and reaction was carried out at 98° to 102° C. for 6 hours, during which water was removed from the reaction system by means of the Deanstark trap.

After completion of the reaction, the reaction mass was cooled and the catalyst was separated by filtration. Thereafter, n-heptane was removed by distillation from the n-heptane solution, containing the desired product, and the residue obtained was purified by column chromatographic separation to obtain 28.3 g of N-(1,2,2,6,6-pentamethyl-4-piperidinyl)-N-benzylglycine(1,2,2,6,6-pentamethyl-4-piperidinyl)ester as a pale yellow liquid. Yield, 60.0% based on N-(1,2,2,6,6-pentamethyl-4-piperidinyl)-N-benzylglycine.

FD-mass analysis: A parent ion peak (471) was confirmed.

| Elementary analysis (for $C_{29}H_{49}N_3O_2$): | | | |
|---|---|---|---|
| | C (%) | H (%) | N (%) |
| Found | 73.15 | 11.10 | 8.90 |
| Calculated | 73.89 | 10.40 | 8.92 |

EXAMPLE 9

To a four-necked flask equipped with a thermometer, a stirrer and a Deanstark trap were added 22.8 g (0.1 mole) of N-(2,2,6,6-tetramethyl-4-piperidinyl)-N-methylglycine, 18.7 g (0.12 mole) of 2,2,6,6-tetramethyl-4-piperidinol, 3.5 g (0.02 mole) of p-toluenesulfonic acid and 100 g of n-octane. The temperature was raised with stirring, and reaction was carried out at 122° to 124° C. for 5 hours, during which water was removed from the reaction system by means of the Deanstark trap.

After completion of the reaction, the reaction mass was cooled with ice, and water was then added thereto with ice-cooling to separate the system into an aqueous and n-octane layers. Thereafter, the n-octane layer was separated and concentrated by removing n-octane therefrom by distillation. The residue obtained was purified by column chromatographic separation to obtain 26.5 g of N-(2,2,6,6-tetramethyl-4-piperidinyl)-N-methylglycine(2,2,6,6-tetramethyl-4-piperidinyl)ester as a pale brown liquid. Yield, 72.5% based on N-(2,2,6,6-tetramethyl-4-piperidinyl)-N-methylglycine.

FD-mass analysis: A parent ion peak (367) was confirmed.

| Elementary analysis (for $C_{21}H_{41}N_3O_2$): | | | |
|---|---|---|---|
| | C (%) | H (%) | N (%) |
| Found | 68.05 | 11.20 | 11.51 |
| Calculated | 68.66 | 11.17 | 11.44 |

EXAMPLE 10

The blend described below was mixed on a mixer for 5 minutes and then melt-kneaded at 180° C. on a mixing roll to obtain a compound. This compound was formed into a sheet of 1 mm in thickness on a hot press kept at 210° C., and test pieces of 150×30×1 mm (thick) were prepared therefrom.

The test piece thus obtained was exposed to light in a Sunshine weather meter (light source, carbon arc; temperature of black panel, 83±3° C.; spraying cycle, 120 minutes; and spraying time, 18 minutes) and bent like lobster every 60 hours to obtain a time required for the test piece to break into two. The weathering resistance was evaluated by this time.

| Compounding: | |
|---|---|
| Unstabilized polypropylene | 100 parts by weight |
| Calcium stearate | 0.1 parts by weight |
| 2,6-Di-tert-butyl-4-methylphenol | 0.05 parts by weight |
| Test compound | 0.15 parts by weight |

The result is shown in Table 2.

In the table, UVA-1 to UVA-5 are compounds shown below, and HA-1 to HA-9 are compounds shown in Table 1.

UVA-1: 2-(2-Hydroxy-3-tert-butyl-5-methylphenyl)-5-chlorobenzotriazole
UVA-2: Bis(2,2,6,6-tetramethyl-4-piperidinyl)sebacate
UVA-3: 4-Benzoyloxy-2,2,6,6-tetramethylpiperidine
UVA-4: N-(2,2,6,6-tetramethyl-4-piperidinyl)iminodiacetic acid bis(2,2,6,6-tetramethylpiperidinyl)ester
UVA-5: 2,2,6,6-Tetramethyl-4-piperidinylaminopropionic acid methyl ester

TABLE 1

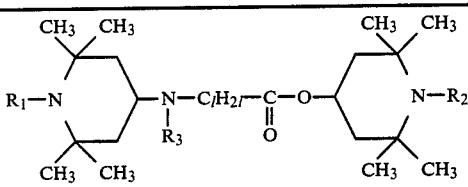

| Example | Compound No. | $R_1$ | $R_3$ | l | $R_2$ |
|---|---|---|---|---|---|
| 1 | HA-1 | H | H | 1 | H |
| 2 | HA-2 | H | n-$C_4H_9$— | 1 | H |
| 3 | HA-8 | H | n-$C_8H_{17}$— | 1 | H |
| 4 | HA-4 | H | n-$C_{11}H_{23}$— | 1 | H |
| 5 | HA-5 | $CH_3$— | H | 1 | $CH_3$— |
| 6 | HA-6 | H | H | 2 | H |
| 7 | HA-7 | $CH_3\overset{\underset{\parallel}{O}}{C}$— | H | 1 | $CH_3\overset{\underset{\parallel}{O}}{C}$— |
| 8 | HA-8 | $CH_3$— |  | 1 | $CH_3$— |
| 9 | HA-9 | H | $CH_3$— | 1 | H |

TABLE 2

| Example | No. | Light stabilizer | Light fastness (hr) |
|---|---|---|---|
| Present Examples | 1 | HA-1 | 1320 |
| | 2 | HA-2 | 1260 |
| | 3 | HA-3 | 1200 |
| | 4 | HA-4 | 1140 |
| | 5 | HA-5 | 1320 |
| | 6 | HA-6 | 1200 |
| | 7 | HA-7 | 1200 |
| | 8 | HA-8 | 1140 |
| | 9 | HA-9 | 1200 |
| Comparative Examples | 10 | UVA-1 | 360 |
| | 11 | UVA-2 | 960 |
| | 12 | UVA-3 | 840 |
| | 13 | UVA-4 | 1080 |
| | 14 | UVA-5 | 1020 |
| | 15 | No addition | 120 |

EXAMPLE 11

The blend described below was extruded and then injection-molded into test pieces of 2 mm in thickness.

The test piece was exposed to light for 1500 hours in a fade meter (light source, ultraviolet carbon arc; and temperature of black panel, 63±3° C.), and the degree of color change was evaluated in terms of a color difference, $\Delta YI$, between the exposed test piece and unexposed one.

The result is shown in Table 3.

| Compounding: | |
|---|---|
| ABS resin | 100 parts by weight |
| Pentaerythritol tetrakis[3-(3,5-di-tert-butyl-4-hydroxyphenyl)propionate] | 0.05 parts by weight |
| Distearyl 3,3'-thiodipropionate | 0.2 parts by weight |
| Test compound | 0.2 parts by weight |

TABLE 3

| Example | No. | Light stabilizer | $\Delta YI$ |
|---|---|---|---|
| Present Examples | 1 | HA-1 | 12.5 |
| | 2 | HA-2 | 13.1 |
| | 3 | HA-3 | 13.4 |
| | 4 | HA-4 | 14.0 |
| | 5 | HA-5 | 12.6 |
| | 6 | HA-6 | 13.5 |
| | 7 | HA-7 | 14.0 |
| | 8 | HA-8 | 13.6 |
| | 9 | HA-9 | 13.3 |
| Comparative Examples | 10 | UVA-1 | 29.5 |
| | 11 | UVA-2 | 28.6 |
| | 12 | UVA-3 | 28.9 |
| | 13 | UVA-4 | 22.5 |
| | 14 | UVA-5 | 25.3 |
| | 15 | No treatment | 44.2 |

What is claimed is:

1. A piperidine compound represented by the general formula (I),

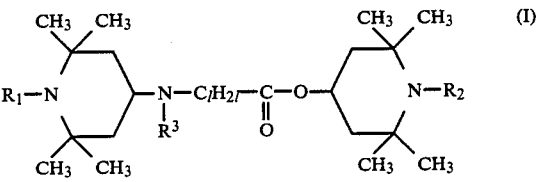

wherein $R_1$ and $R_2$ independently represent a hydrogen atom or a $C_1$-$C_3$ alkyl or $C_2$-$C_{20}$ carbonyl group, $R_3$ represents a hydrogen atom or a $C_1$-$C_{20}$ alkyl, $C_6$-$C_{20}$ aryl, $C_7$-$C_{20}$ aralkyl or $C_2$-$C_{20}$ acyl group, and l represents 1 to 3.

2. A piperidine compound selected from the group consisting of N-(2,2,6,6-tetramethyl-4-piperidinyl)-glycine(2,2,6,6-tetramethyl-4-piperidinyl)ester; N-(2,2,6,6-tetramethyl-4-piperidinyl)-N-n-butyl-glycine(2,2,6,6-tetramethyl-4-piperidinyl)ester; N-(2,2,6,6-tetramethyl-4-piperidinyl)-N-octyl-glycine(2,2,6,6-tetramethyl-4-piperidinyl)ester; N-(2,2,6,6-tetramethyl-4-piperidinyl)-N-undecanyl-glycine(2,2,6,6-tetramethyl-4-piperidinyl)ester; N-(1,2,2,6,6-pentamethyl-4-piperidinyl)glycine(1,2,2,6,6-pentamethyl-4-piperidinyl)ester; N-(2,2,6,6-tetramethyl-4-piperidinyl)aminopropionic acid (2,2,6,6-tetramethyl-4-piperidinyl)ester; N-(1-acetyl-2,2,6,6-tetramethyl-4-piperidinyl)glycine(1-acetyl-2,2,6,6-tetramethyl-4-piperidinyl)ester; N-(1,2,2,6,6-pentamethyl-4-piperidinyl)-N-benzylglycine(1,2,2,6,6-pentamethyl-4-piperidinyl)ester and N-(2,2,6,6-tetramethyl-4-piperidinyl)-N-methylglycine(2,2,6,6-tetramethyl-4-piperidinyl)ester.

3. A method for producing a piperidine compound represented by the formula (I),

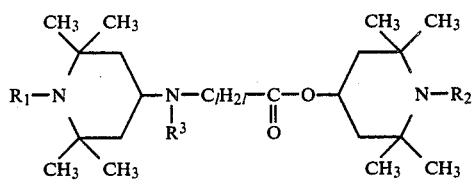

wherein $R_1$ and $R_2$ independently represent a hydrogen atom or a $C_1$–$C_3$ alkyl or $C_2$–$C_{20}$ carbonyl group, $R_3$ represents a hydrogen atom or a $C_1$–$C_{20}$ alkyl, $C_6$–$C_{20}$ aryl, $C_7$–$C_{20}$ aralkyl or $C_2$–$C_{20}$ acyl group, and l represents 1 to 3, characterized in that a carboxylic acid compound represented by the formula (II),

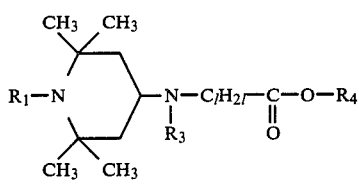

wherein $R_1$, $R_3$ and have the same meanings as described above, and $R_4$ represents a hydrogen atom or a $C_1$–$C_3$ alkyl group, is reacted with a piperidinol represented by the formula (III),

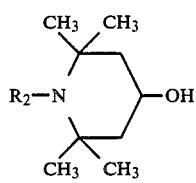

wherein $R_2$ has the same meaning as described above and wherein the piperidinol of the formula (III) is used in an amount of 0.9 to 2 mols per 1 mol of the carboxylic acid of the formula (II).

4. A method as claimed in claim 3 wherein the reaction is carried out in the presence of a basic or acid catalyst.

5. A method as claimed in claim 4 wherein the basic catalyst is selected from the group consisting of metal hydroxides, metal hydrides, metal amides, alkali metal alkoxides and alkali metal phenoxides.

6. A method as claimed in claim 4 wherein the acid catalyst is selected from the group consisting of mineral acids, aromatic sulfonic acids and aliphatic sulfonic acids.

7. A method as claimed in any of claims 4 to 6 wherein the catalyst is used in an amount of 0.05 to 1.20 mols based on 1 mol of the compound of the formula (II).

8. A method as claimed in claim 3 wherein the piperidinol of the formula (III) is used in an amount of 1.0 to 1.5 mols based on 1 mol of the carboxylic acid derivative of the formula (II).

9. A method as claimed in claim 3 wherein the reaction is carried out at a temperature in the range of from 50° C. to 200° C.

10. A stabilizer for organic material containing as an effective ingredient a piperidine compound represented by the formula (I),

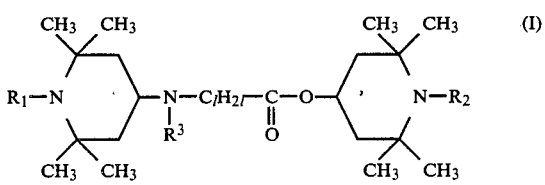

wherein $R_1$ and $R_2$ independently represent a hydrogen atom or a $C_1$–$C_3$ alkyl or $C_2$–$C_{20}$ acyl group, $R_3$ represents a hydrogen atom or a $C_1$–$C_{20}$ alkyl, $C_6$–$C_{20}$ aryl, $C_7$–$C_{20}$ aralkyl or $C_2$–$C_{20}$ carbonyl group, and l represents 1 to 3.

11. A stabilized organic material containing a piperidine compound represented by the formula (I),

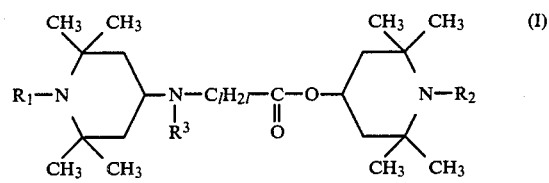

wherein $R_1$ and $R_2$ independently represent a hydrogen atom or a $C_1$–$C_3$ alkyl or $C_2$–$C_{20}$ acyl group, $R_3$ represents a hydrogen atom or a $C_1$–$C_{20}$ alkyl, $C_6$–$C_{20}$ aryl, $C_7$–$C_{20}$ aralkyl or $C_2$–$C_{20}$ carbonyl group, and l represents 1 to 3.

12. A stabilized organic material as claimed in claim 11 wherein the organic material is a paint.

13. A stabilized organic material as claimed in claim 11 wherein the organic material is a polyolefine.

14. A stabilized organic material as claimed in claim 13 wherein the polyolefine is selected from the group consisting of polyethylene and polypropylene.

* * * * *